United States Patent [19]

Kalopissis et al.

[11] 3,984,569

[45] Oct. 5, 1976

[54] COSMETIC COMPOSITIONS FOR TREATING THE HAIR CONTAINING S-SUBSTITUTED DERIVATIVES OF GLUTATHIONE

[75] Inventors: Gregoire Kalopissis, Paris; Claude Bouillon, Eaubonne, both of France

[73] Assignee: L'Oreal, France

[22] Filed: Sept. 11, 1972

[21] Appl. No.: 287,701

[30] Foreign Application Priority Data

Sept. 20, 1971 Luxemburg ..............................63924/71

[52] U.S. Cl................................. 424/319; 424/315
[51] Int. Cl.².......................................... A61K 31/195
[58] Field of Search................... 424/177, 319, 315; 260/112.5

[56] References Cited
OTHER PUBLICATIONS

Chemical Abstracts, Watambe et al. 70:58286j (1969).
Abstract of Japanese Patent No. 42-1535 (1967).
Surikov et al. — Chem. Abst. vol. 56 (1962), p. 10665h.
Chem. Abst., 8th Collective Index vol. 66–75 (1967–1971), p. 13956s.

*Primary Examiner*—Leonard Schenkman
*Attorney, Agent, or Firm*—Cushman, Darby & Cushman

[57] ABSTRACT

A composition and method for treating the scalp and skin characterized by an excessive secretion of sebum, to improve the condition thereof and to reduce a greasy and unaesthetic appearance of the hair comprising topically applying to the scalp or skin or orally administering to a person having a scalp or skin so characterized, a composition containing effective amounts of S-substituted derivatives of glutathione as the active component in said composition.

3 Claims, No Drawings

COSMETIC COMPOSITIONS FOR TREATING THE HAIR CONTAINING S-SUBSTITUTED DERIVATIVES OF GLUTATHIONE

The present invention relates to composition and method for combatting the greasy and unaesthetic appearance of the hair, to a composition and method for improving the appearance of the skin, said composition susceptible of being employed topically or orally, and to certain compounds usefully employed in said compositions and methods.

More particularly, the present invention relates to a composition and to a method for treating the scalp and skin characterized by an excessive secretion of sebum, to improve the condition thereof by reducing said excessive secretion, thereby effectively and substantially reducing or eliminating a greasy appearance of the hair and an unaesthetic appearance of the skin, by topically applying to the skin or scalp of a human having a scalp or skin so characterized, a composition containing a S-substituted derivative of glutathione, as the active agent, in amounts effective to substantially reduce or eliminate said greasy or unaesthetic appearance; or by orally administering to a human having a scalp or skin so characterized a therapeutic composition comprising an ingestible carrier admixed with, as a non-toxic active compound, said S-substituted derivative of glutathione, in amounts effective to substantially reduce or eliminate said greasy or unaesthetic appearance.

These compositions exhibit very good stability characteristics, are non-toxic and exhibit no aggressiveness to the scalp or skin.

The active compound employed in the present invention is selected from the group consisting of a compound of the formula

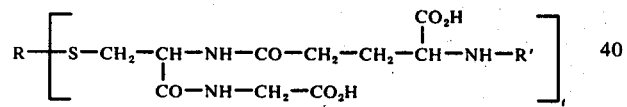

and the acid salts thereof, wherein R' is selected from the group consisting of hydrogen, —$CONH_2$ and —COA wherein A is selected from the group consisting of alkyl having 1 – 18 carbon atoms and alkenyl having 2 to 18 carbon atoms, and t is 1 or 2 and a. when $t = 1$, R is selected from the group consisting of:
1. linear or branched alkyl having from 1 to 18 carbon atoms,
2. alkenyl having from 3 to 18 carbon atoms,
3. alkyl having from 2 to 4 carbon atoms and substituted by one or two OH groups,
4.

wherein $m$ is 1 or 2 and R'' is lower alkyl having 1—4 carbon atoms,

5.

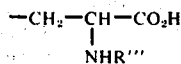

wherein R''' is selected from the group consisting of —$CONH_2$ and —COA wherein A has the meaning given above, 6. —$(CH_2)_n$—NH—$R_1$, wherein $n$ is 2 or 3 and $R_1$ is selected from the group consisting of hydrogen, —$CONH_2$, —$COR_2$ and —$SO_2R_3$ wherein $R_2$ is selected from the group consisting of hydrogen, alkyl having 1 – 18 carbon atoms, alkenyl having 2 to 18 carbon atoms, —$CF_3$,

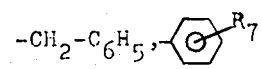

wherein $R_7$ is selected from the group consisting of hydrogen, alkyl, alkyl having 1 – 4 carbon atoms, alkoxy having 1 – 4 carbon atoms and halogen and $R_3$ is selected from the group consisting of alkyl having 1 – 4 carbon atoms and

wherein $R_7$ has the meaning given above,

7. —$(CH_2)_p$—$R_4$ wherein $p$ is 0, 1 or 2 and $R_4$ is selected from the group consisting of
   i. 1-naphthyl when $p = 0$ or 1,
   ii. 2-naphthyl when $p = 0$ or 1,
   iii. 2-thienyl when $p = 1$,
   iv. 1,2-tetrahydrofuryl when $p = 1$,
   v. 2-furyl when $p = 1$,
   vi. 2-pyridyl when $p = 0$, 1 or 2,
   vii. 2-pyridyl substituted by a member selected from the group consisting of nitro and alkyl having 1 –4 carbon atoms when $p = 0$, 1 and 2,
   viii. 2-pyridyl N-oxide when $p = 0$, 1 or 2 and

when $p = 0$, 1 or 2, wherein $q$ is 1, 2 or 3 and
a'. when $q$ is 1, 2 or 3, $R_5$ is selected from the group consisting of hydrogen, halogen, alkoxy having 1 – 5 carbon atoms and alkyl having 1 – 4 carbon atoms and b'. when $q$ is only 1, $R_5$ is selected from the group consisting of dialkylamino wherein the alkyl moiety has 1 – 3 carbon atoms, phenoxy, cyclohexyl, amino, methylenedioxy, phenyl, alkylthio wherein the alkyl moiety has 1 –5 carbon atoms, alkylsulfinyl wherein the alkyl moiety has 1 – 5 carbon atoms and trifluoromethyl, 8. — $CH_2$ — $CH_2$ — $CH_2$ — $C_6H_5$,
9. — $CH(C_6H_5)_2$,
10. — $CH_2$ — $CH = CH$ — $C_6H_5$,
11. — $CH$ — $(C_6H_4p$ — $OCH_3)_2$
12. — $C(CH_3)_2$ $(C_6H_4p$ — $OCH_3)$,
13. — $(CH_2)_s$ — $(OR_6)$
wherein $s$ is an integer of 1–4 and $R_6$ is selected from the group consisting of OH, morpholino, pyrrolidino, N-methyl piperazino, $NH_2$, diethylamino and dimethylamino, and
14. 1,2-dicarboxy ethyl b. when $t = 2$, R is selected from the group consisting of
15. —$(CH_2)_n$ — $CH_2$— wherein $n$ is 1, 2 or 3,
16. —$(CH_2)_n$ — $CH_2$— wherein $n$ is 1, 2 or 3 and substituted by 1 or 2 OH functions,
17. butenylene, and
18. —$(CH_2)_2$ —$SO_2$ —$(CH_2)_2$—.

The compounds according to the invention as indicated above can advantageously be used in the form of their salts, with an inorganic or organic acid when these compounds comprise at least a primary amine group. However, since the carboxylic acid functions of the glutathione molecule give rise, with the primary amine functions possibly present in the molecule, to the formation of an internal salt, the corresponding salt can be obtained only by using a strong acid, which can, for example, be an inorganic acid such as hydrochloric, hydrobromic, sulfuric and phosphoric acid or else paratoluene-sulfonic or trichoracetic acid.

Representative compounds usefully employed in the composition of the present invention included:

S-(o-fluorobenzyl) glutathione,
S-(2-pyridyl N-oxide) glutathione,
S-[(2)-2-pyridyl ethyl] glutathione,
S,S'-(2,2'-sulfonyl diethyl) diglutathione,
S-(1,2-dicarboxy ethyl) glutathione,
S-isopropyl glutathione,
S-n-octyl glutathione,
S-dodecyl glutathione,
S-hexadecyl glutathione,
S-octadecyl glutathione,
S-(octadecene-9 yl) glutathione,
S-allyl glutathione,
S-(2,2-dimethoxy ethyl) glutathione,
S-(β-ureidoethyl) glutathione,
S-(β-aminoethyl) glutathione,
S-(2-naphthyl) glutathione,
S,S'-(2,3-dihydroxy 1,4-butanediyl) diglutathione,
S-benzyl glutathione,
S-(p-methoxybenzyl) glutathione,
S-(p-fluorobenzyl) glutathione,
S-)p-chlorobenzyl) glutathione,
S-(p-bromobenzyl) glutathione,
S-(m-chlorobenzyl) glutathione,
S-(2-pyridyl methyl) glutathione,
S-(β-phenylethyl) glutathione,
S-(p-diphenylmethyl) glutathione,
S-(2-thenyl) glutathione,
S-piperonyl glutathione,
S-(β-carboxyethyl) glutathione,
S-(o-tolyl)glutathione,
S-(carboxymethyl) glutathione,
S-(p-butoxybenzyl) glutathione,
S-(p-phenoxybenzyl) glutathione,
S-(γ-phenylpropyl) glutathione,
S-(β-phenylacetamidoethyl) glutathione,
S-(m-chlorobenzamidoethyl) glutathione,
S-phenyl glutathione,
S-(cyclohexylbenzyl) glutathione,
S-benzyl N-carbamyl glutathione,
S-(3,4-dimethoxy benzyl) N-acetyl glutathione,
S-(2,4-dichloro benzyl) N-propionyl glutathione,
S-(β-nicotinamidoethyl) glutathione,
S-decyl glutathione,
S-β-hydroxyethyl glutathione,
S-(3,3-ethylenedioxy propyl) glutathione,
S-(3,3-diethoxy propyl) glutathione,
S-(2-carboxy 2-octadedanamido ethyl) glutathione,
S-(2-carboxy 2-ureido ethyl) glutathione,
S-(2-carboxy 2-hexadecanamido ethyl) glutathione,
S-[2-carboxy 2-(9-octadecene amido) ethyl] glutathione,
S-(2-carboxy 2-propionamido ethyl) glutathione,
S-[2-(10-undecene amido) ethyl] glutathione,
S-(2-trifluoracetamido ethyl) glutathione,
S-(methane 2-sulfonamido ethyl) glutathione,
S-(2-p-toluenesulfonamido ethyl) glutathione,
S-furfuryl glutathione,
S-(5-nitro 2-pyridyl) glutathione,
S-p-methylsulfinylbenzyl glutathione,
S-p-butylthiobenzyl glutathione,
S-(2-tetradecanamido ethyl) glutathione,
S-pyrrolidinocarbonylmethyl glutathione,
S-carbamoylmethyl glutathione,
S-(2-diethylaminocarbonyl ethyl) glutathione and
S-octyl N-hexadecanoyl glutathione.

I. Topically Applied Compositions

In accordance with the present invention, there is provided a variety of compositions which can be topically applied to the scalp or skin to achieve the aforementioned result and these compositions include said active compound in amounts generally between 0.1 and 5, and preferably between 1 and 3 percent by weight of said composition.

For instance capillary compositions made in accordance with the present invention can contain one or more active compounds previously defined by the general formula, or in admixture with other already known compounds for combatting the greasy and unaesthetic appearance of the hair. These capillary compositions, according to the invention, can also contain ingredients such as penetrating agents or perfumes which are generally used in cosmetics.

The present invention also has for its object a process for treating hair to improve its appearance, a process essentially characterized by the fact the capillary product, as defined above, is applied to the hair.

The cosmetic compositions, according to the invention, can also take the form of hair setting lacquers or lotions containing at least one active compound in combination in a suitable cosmetic vehicle in amounts as defined above with at least a conventional film forming cosmetic resin having a molecular weight ranging from about 10,000 to 3,000,000 in amounts of about 1 – 20 percent by weight of said composition.

Representative cosmetic resins that can be used, there can be cited in particular: polyvinylpyrrolidone having a molecular weight between 10,000 and 70,000; 70–30%/30–70% vinylpyrrolidone/vinyl acetate copolymers; copolymers of vinyl acetate and an unsaturated carboxylic acid such as crotonic acid (molecular weight — 20,000); copolymers resulting from the polymerization of vinyl acetate (75–85%), crotonic acid (5–15%) and an acrylic or methacrylic ester (5–15%) or an alkyl vinyl ether (5–15%); copolymers resulting from the copolymerization of vinyl acetate (63–88%), crotonic acid (5–15%) and a. (5–25%) of a vinyl ester of an acid with a long carbon chain having 10 to 22 carbon atoms or b. (5–25%) of an allyl or methallyl ester of an acid with a long carbon chain having 10 to 22 carbon atoms; copolymers resulting from the copolymerization of 65–80% of an ester of an unsaturated alcohol having from 2 to 12 carbon atoms and a carboxylic acid having from 2 to 15 carbon atoms, 7–12% of an unsaturated acid having from 4 to 20 carbon atoms and 10–20% of at least an ester of a saturated alcohol having from 8 to 18 carbon atoms and an unsaturated acid having from 4 to 20 carbon atoms. In a particular embodiment, the cosmetic resin contained in the composition according to the invention can have side chains at whose end is a thiol function.

The cosmetic resin utilized in the composition of the present invention which is in the form of a hair setting lotion or lacquer can also be made up of colored polymers, i.e., polymers containing in their macromolecular chain dye molecules which make it possible to give the hair a coloring or particular shade.

Additionally, these capillary compositions can also contain direct dyes intended to cause a dyeing or shading of the hair and they can also contain other standard cosmetic components or adjuvants such as penetrating agents, surfactants, dyes, perfumes, etc.

The cosmetic vehicle utilized in these capillary compositions can be made up of standard mixtures used for making hair setting lotions or lacquers or again hair dressing compositions. Thus, these cosmetic compositions can comprise a solution of said active component in a solvent such as water, a lower alkanol or an aqueous solution of a lower alkanol wherein the lower alkanol is present in amounts of about 20 to 70 weight percent thereof. The choice of solvent for the active ingredient or component can depend on a number of easily ascertainable factors such as the particular active component chosen, its solubility characteristics, the ultimate use of the composition and the like. When a lower alkanol, alone or as an aqueous solution thereof, is selected, generally the alkanol is ethanol or isopropanol.

When the capillary compositions of the present invention are employed in aerosol form, generally the active component is present as a solution thereof in a lower alkanol, together with a conventional aerosol propellant such as a fluoronated hydrocarbon including dichlorodifluoromethane, trichloromonofluoromethane and mixtures thereof. Obviously, other well-known propellants can also be used. Generally, the propellant is present in amounts of about 66 to 75 weight percent of the total aerosol composition, which is, of course, packaged under pressure.

In these aerosol compositions which also include a film forming resin, the concentration of active component is generally from 0.1 to 5 weight percent thereof and preferably between 1 and 3%, while the resin concentration is preferably between 1 and 20% by weight.

The use of the capillary compositions of the present invention makes it possible to treat the hair while subjecting it to a setting operation, this process being essentially characterized by the fact that the hair is impregnated with a composition containing in combination the active compound with a cosmetic film forming resin, that the hair is put up on rollers and allowed to dry.

The cosmetic compositions according to the invention also can take the form of a shampoo formulation which effectively reduces or essentially eliminates greasy and unaesthetic appearance of the hair.

These shampoo compositions are essentially characterized by the fact that they contain, in combination, at least one anionic, cationic, non-ionic or amphoteric detergent with at least an active compound such as defined above in amounts as also defined above.

Representative anionic detergents include alkyl sulfates, alkylether sulfates, alkylpolyether sulfates, alkyl sulfonates (the alkyl groups having from 8 to 18 carbon atoms), sulfated monoglycerides, sulfonated monoglycerides, sulfated alkanolamides, sulfonated alkanolamides, fatty acid soaps, fatty alcohol monosulfosuccinates, the products of condensation of fatty acids with isethionic acid, the products of condensation of fatty acids with methyltaurine, the products of condensation of fatty acids with sarcosine, the products of condensation of fatty acids with a hydrolysate of proteins.

Representative cationic detergents include long chain quaternary ammoniums, the esters of fatty acids and amino alcohols and polyether amines. Specifically such cationic detergents as dilauryldimethyl ammonium chloride, diisobutyl phenoxy ethoxy ethyl dimethylbenzyl ammonium chloride, cetyl trimethyl ammonium bromide, N-cetyl pyridinium bromide and benzethonium chloride, lauryl benzyl trimethyl ammonium bromide or chloride, myristyl benzyl trimethyl ammonium bromide or chloride and cetyl benzyl trimethyl ammonium bromide or chloride can be used.

Suitable examples of non-ionic detergents include esters of polyols and sugars, the products of condensation of ethylene oxide on fatty acids, on fatty alcohols, on long chain alkylphenols (e.g. octadecyl phenol), on long chain mercaptans, on long chain amides and polyethers of polyhydroxyl fatty alcohols such as lauryl alcohol oxyethylenated with 12 moles of ethylene oxide and $C_{12}$ thiols oxyethylenated with 12 moles of ethylene oxide.

Representative amphoteric detergents such as asparagine derivatives, the products of condensation of monochloracetic acid on imidazolines, alkylamino propionates, wherein the alkyl moiety contains 10 – 20 carbon atoms and compounds having the formula

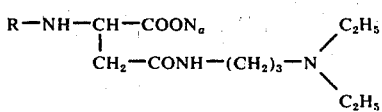

wherein R is a radical derived from fatty acids of copra and radicals ($C_8$ and $C_{20}$) derived from tallow.

These shampoo compositions generally contain from 0.1 to 5%, preferably from 1 to 3%, of the active component as defined above. They also contain, for example, from 4 to 15%, preferably from 5 to 7%, by weight of said detergents in solution in an aqueous medium and have a pH generally ranging from about 3 – 8.

The shampoos as defined above can also contain other usual cosmetic ingredients, such as perfumes and dyes. They can also contain thickeners such as fatty acid alkanolamides, cellulose derivatives (for example, carboxymethyl cellulose and hydroxymethyl cellulose) long chain polyol esters and natural gums, so as to be in the form of a cream or gel. Finally, these shampoos can be in the form of powders intended either to be applied to wet hair or be dissolved in a certain volume of water before washing of the hair. Additionally, the shampoo compositions of this invention can also contain dyes intended to dye the hair.

These compositions in the form of shampoos make it possible to use a process to combat the greasy and unaesthetic appearance of the hair, this process comprising applying to the hair, possibly previously wetted, a useful amount, generally about 10 – 20 cm$^3$, of a shampoo as defined above, massaging the scalp from one to several minutes and then rinsing the hair. Generally, a satisfactory result is obtained by a weekly shampooing, which makes it possible to reduce, and in certain cases, to eliminate the greasy appearance of the hair, while also assuring normal maintenance of the hair.

Yet another topically applied composition including the active compounds of the present invention is a formulation for use in effecting a permanent wave or deformation of hair exhibiting a greasy and unaesthetic appearance.

In one embodiment of the use of such permanent wave formulations, the hair is permanently waved by applying to the hair wound on curlers during the first stage, i.e., during the reducing stage, a cosmetic composition comprising a mixture of a reducing agent and the active compound of this invention as defined above, permitting the composition to remain on the hair for a time sufficient to alter the disulphide bonds of the keratin of the hair, generally about 10 to 40 minutes, thoroughly rinsing the hair to remove residual reducing agent and applying in the second stage, i.e., during the neutralization stage, an oxidizing or neutralizing agent to reform the disulphide bonds of the keratin of the hair.

In another embodiment of using these permanent wave formulations the hair is permanently waved by applying to the hair wound on curlers during the first stage, i.e. during the reducing stage, a reducing agent, permitting the composition to remain on the hair for a time sufficient to alter the disulphide bonds of the keratin of the hair, generally about 10 to 40 minutes, thoroughly rinsing the hair to remove residual reducing agent and applying in the second stage, i.e., during the neutralization stage, a cosmetic composition comprising a mixture of an oxidizing or neutralizing agent and the active compound as defined hereinbefore whereby the disulphide bonds of the keratin of the hair are reformed.

In an alternative procedure the hair is permanently waved in a single stage by impregnating the hair wound on curlers with a cosmetic composition comprising a mixture of a thiol reducing agent for altering the disulphide bonds of the keratin of the hair, an organic disulphide and the active compound of the present invention, the molar ratio of said organic disulphide to said thiol being greater than 1, and as high as about 20, permitting the composition to remain on the hair for a time sufficient to induce a permanent wave therein, generally about 10 to 40 minutes, and unwinding the hair from the curlers. Conventional separate neutralization operations are not required in the practice of this embodiment of the invention.

The active compound of this invention used in these permanent wave formulations can be admixed with a conventional reducing agent and is present in the resulting mixture in amounts between 0.1 to 5% by weight of the total and preferably between 1 and 3 weight percent. The pH of this cosmetic composition is preferably between 3 and 9.5. Conventional reducing agents employed are advantageously those organic thiols which are generally used to perform the first stage of a permanent waving operation. Representative thiols include thioglycolic acid, ammonium thioglycolate, thioglycerol, thiolactic acid, thioglycolic amide or hydrazide or the like.

Conveniently, and also in accordance with the present invention, the reducing composition is a twopackage composition, the first package containing a thiol reducing agent as described above and the second package containing the active compound of this invention in amounts such that when the contents of the two packages are mixed together, preferably just before initiation of the reducing operation, the resulting reducing composition contains said active compound in amounts of about 0.1 – 5 weight percent of the total mixture.

Alternatively, the said active compound is admixed with a conventional neutralizing or oxidizing agent and is present in the resulting mixture in amounts between 0.1 to 5 weight percent, and preferably between 1 and 3 weight percent of the total. Conventional neutralizing agents employed include, for instance, hydrogen peroxide, sodium or potassium bromate, sodium perborate or percarbonate and the like.

Conveniently also, the neutralizing composition is a two-package composition, the first package containing the neutralizing agent as described above and the second package containing said active compound also as defined above in amounts such that when the contents of the two packages are mixed together, preferably just before initiation of the neutralization operation, the resulting neutralizing composition contains the active compound in amounts of about 0.1 –5 weight percent of the total mixture.

As a further alternative, the active compound is admixed with a single stage permanent hair waving agent, and is present in the resulting mixture in amounts between 0.1 – 5 weight percent, preferably, between about 1 and 3 weight percent of the total. Conventional single stage permanent hair waving agents can be employed and include a mixture of an organic disulfide and a thiol, the mol ratio of the disulfide to the thiol being greater than 1.

Suitable thiols include thioglycolic acid, glycol thioglycolate, glycerol thioglycolate, β-mercaptoethanol, N-carboxymethyl-mercaptoacetamide, glycol thiolactate and the like.

As the organic disulphides there can be used the disulphides of the thiols set forth in the preceding paragraph. For instance glycol dithiodiglycolate, glycerol dithioglycolate, glycol dithiodiolactate, dithiodiethanol and N-carboxymethyldithioacetamide can be employed. Additional ingredients can include ammonia, water, urea and lower alkanols in conventionally employed amounts and the pH of the single stage permanent hair waving composition ranges between about 8 – 10, preferably about 8.5 to 9.5. Typical formulations of such single stage permanent hair waving agents are disclosed in French Pat. Nos. 1,443,888 and 1,455,788.

Again, conveniently, the single stage permanent hair waving composition is a two-package composition, the first package containing the single stage permanent hair waving agent and the second package containing the active compound, as defined above, in amounts such that when the contents of the two packages are mixed together, preferably just before use, the resulting permanent hair waving composition contains the active compounds in amounts of about 0.1 – 5 weight percent of the total mixture.

As will be recognized, these permanent wave formulations can also include other additives conventionally employed such as penetrating agents, surfactants, dyes or perfumes and can be admixed with conventional vehicles such as water, lower alkanols and their mixtures as defined above. Further, they can be provided in the form of a solution, a foam, a cream or gel and can be provided in the form of a sprayable aerosol especially when the cosmetic vehicle is water, lower alkanol or their mixtures. The sprayable aerosol can include an amount of a liquefied gas under pressure, such as a flurochlorinated hydrocarbon, also as defined hereinbefore.

In yet another embodiment of the present invention, a dermal lotion composition can be provided which contains as the active ingredient the compound defined above present in amounts of about 0.1 – 5 percent by weight of said composition.

Such dermal compositions which can be topically applied to the skin are preferably in the form of creams, milks, gels, dermatological cakes or aerosol foams. These compositions can also be in the form of aqueous or dilute alcohol lotions. In addition, these dermal compositions can contain conventional ingredients such as fatty bodies, emulsifiers, preservatives, perfumes, dyes, waxes. They can also contain colored pigments which make it possible to dye or color the skin and hide skin defects.

II Orally Administered Compositions

In accordance with another embodiment of the present invention, there is provided a composition and method for treating a scalp characterized by an excessive secretion of sebum, to improve the condition thereof by reducing said excessive secretion which comprises orally administering to a human being having a scalp so characterized a therapeutic composition comprising an ingestible carrier admixed with, as a non-toxic active ingredient, an active compound as defined above.

This embodiment has numerous advantages, in particular, for women as it makes it possible to treat greasy hair without having to topically apply a composition containing said active compound to the scalp which could disturb the hairdo.

These oral compositions generally contain the said active compound in a concentration of about 0.01 to 50 percent and preferably between about 1 to 10 percent by weight. The active compound can be incorporated in a liquid food such as an aqueous or dilute non-toxic lower alkanol, such as ethanol, which can be optionally flavored or it can be incorporated in an ingestible solid excipient and be provided in the form of granules, pills, tablets or lozenges. The active compound can also be packaged in ingestible capsules and the capsules incorporated into a liquid food. It has been determined that the active compounds of this invention are non-toxic which makes them useful in such orally administrable compositions.

These compositions, whether in liquid or solid form, can be orally administered at a rate of about 100 mg/24 hours and can be administered for successive periods of 15 days with an interruption of 15 days, thereafter the treatment can be resumed, if necessary or desirable.

III New Compounds

The present invention is also directed to the following new compounds: S-(o-fluorobenzyl) glutathione, S-(2-pyridyl N-oxide) glutathione, S-[(2)-2-pyridyl ethyl] glutathione, S,S'-(2,2'-sulfonyl diethyl) diglutathione, S-(1,2-dicarboxy ethyl) glutathione, S-isopropyl glutathione, S-dodecyl glutathione, S-hexadecyl glutathione, S-octadecyl glutathione, S-(octadecene-9 yl) glutathione, S-allyl glutathione, S-(2,2-dimethoxy ethyl) glutathione, S-($\beta$-ureidoethyl) glutathione, S-($\beta$-aminoethyl) glutathione, S-(2-naphthyl) glutathione, S,S'-(2,3-dihydroxy 1,4-butanediyl) glutathione, S-(2-pyridyl methyl) glutathione, S-(diphenylmethyl) glutathione, S-(2-thenyl) glutathione, S-piperonyl glutathione, S-($\beta$-carboxyethyl glutathione, S-(o-tolyl) glutathione, S-(p-butoxybenzyl) glutathione, S-(p-phenoxybenzyl) glutathione, S-($\beta$-phenyl acetamidoethyl) glutathione, S-(m-chlorobenzoamido ethyl) glutathione, S-(cyclohexylbenzyl) glutathione, S-benzyl N-carbamyl glutathione, S-(3,4-dimethoxy benzyl) N-acetyl glutathione, S-(2,4-dichloro benzyl) N-propionyl glutathione, S-($\beta$-nicotinamidoethyl) glutathione, S-decyl glutathione, S-$\beta$-hydroxyethyl glutathione, S-(3,3-ethylenedioxy propyl) glutathione, S-(3,3-diethoxy propyl) glutathione, S-(2-carboxy 2-octadecanamido ethyl) glutathione, S-(2-carboxy 2-ureido ethyl) glutathione, S-(2-carboxy 2-hexadecanamido ethyl) glutathione, S-[2-carboxy 2-(9-octadecene amido) ethyl] glutathione, S-(2-carboxy 2-propionamido ethyl) glutathione, S-[2-(10-undecene amido) ethyl] glutathione, S-(2-trifluoracetamido ethyl) glutathione, S-(methane 2-sulfonamido ethyl) glutathione, S-(2-p-toluenesulfonamido ethyl) glutathione, S-furfuryl glutathione, S-(5-nitro 2-pyridyl) glutathione, S-p-methylsulfinylbenzyl glutathione, S-p-butylthiobenzyl glutathione, S-(2-tetradecanamido ethyl) glutathione, S-pyrrolidinocarbonyl methyl glutatione, S-carbarnoylmethyl glutathione, S-(2-diethylaminocarbonyl ethyl) glutathione and S-octyl N-hexadecanoyl glutathione.

IV Methods of Preparation of Active Compounds

In a general manner, the active compounds of the present invention can be prepared by the reaction of glutathione (GSH), with an organic halide or with an ester of methane sulfonic acid and of p-toluene sulfonic acid (method A), or with a compound having a reactive double bond (method B), or with an alcohol (method C), or with ethylene imine and its derivatives of acylation or sulfonylation (method D) or with an oxirane (method D2).

Method A

The most commonly employed process is the substitution reaction of essentially an equimolar ratio of glutathione with an organic halide or a mesylate or a tosylate. The reaction is performed under the conditions usually required for nucleophilic substitutions such as at a temperature of about 20° to 90°C and at atmospheric pressure with the solvent being water, alcohol, dioxane, or dimethyl formamide or again a mixture of these materials. The reaction is carried out in the presence of a base such as ammonia, a hydroxide, a carbonate, an alkaline or alkaline earth alcoholate or again an aliphatic amine such as triethylamine or diethylamine according to the following general reaction:

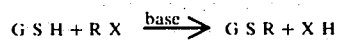

( X = Hal, — $OSO_2CH_3$ or — $OSO_2C_6H_4$-$pCH_3$)

Method A2

When R in RX is aryl ($p = 0$), the halide used is a aryldiazonium halide (Vigneaud et al., J. Biol. Chem., 1941, 138, 369 and Clarke and Inouye, J. Biol. Chem 1931, 94, 541) and the reaction follows the general equation:

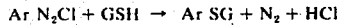

Method B

The addition reaction of essentially an equimolar ratio of glutathione with a compound having a reactive double bond can be carried out without a catalyst or in the presence of a peroxide such as ascaridole, benzoyl peroxide, azo (bis-isobutyrnonitrile), or in the presence of a base as in method A. Most often the reaction is carried out in alcohol, water, dioxane, alone or in admixture. The reactive double bond compound does not contain an amine function, but it can, on the other hand, contain an amide or sulfonamide function. The reaction is generally carried out at a temperature of about 10 to 100°C and at atmospheric pressure in accordance with the following reaction scheme.

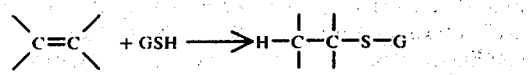

Method C

The compounds according to the invention, which comprises a disubstituted, trisubstituted, benzyl or allyl carbon at a position alpha to the sulfur atom can be prepared by the reaction of essentially an equimolar ratio of the corresponding tertiary, secondary, benzyl or allyl alcohol, with glutathione, in the presence of a strong acid such as gaseous hydrochloric acid, paratoluene-sulfonic acid or a Lewis acid such as boron trifluoride etherate, at a temperature of about 50° to 150°C at atmospheric pressure in accordance with the following general reaction:

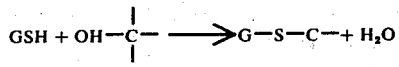

Method D

Another particularly useful method for preparing compounds of the present invention consists of reacting essentially equimolar amounts of glutathione with an ethylene imine or an acylation or N-sulfonylation derivative thereof at a temperature ranging from about -30 to 80°C at ambient or atmospheric pressure according to the following reaction scheme:

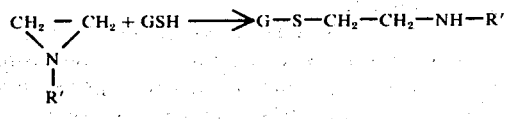

Method D2

The β-hydroxythioethers can be prepared in a similar way by replacing the ethylene imine with an oxirane and by effecting the reaction in a polar medium with a base catalyst, as in method A, according to the following scheme:

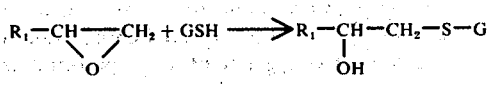

For a better understanding of the invention, there will now be given, by way of examples and without any limiting character, examples of preparing active compounds according to the invention and the various examples of compositions.

REPRESENTATIVE EXAMPLES OF PREPARING ACTIVE COMPOUNDS ACCORDING TO THE FOREGOING GENERAL REACTIONS

EXAMPLE 1

Preparation of S-(o-fluorobenzyl) glutathione

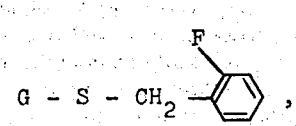

wherein G = glutathione residue

A mixture of 3.07 g of glutathione, 2.8 cc of triethylamine and 100 cc of methanol is brought to a boil. Then a solution of 1.45 g of o-fluorobenzyl chloride in 20 cc of methanol is added. After this addition, the resulting mixture is heated for 3 hours at 50°C, then allowed to cool and, by addition of dilute hydrochloric acid, 3.35 g of a white product are precipitated which can then be crystallized in water. Thus a product having a melting point of around 200°C (with decomposition) is obtained.

By chromatography on paper in a phenol-water medium, there is obtained an $R_f = 0.80$.

Analysis: $C_{17}H_{22}FN_3O_6S$
Calculated %   C 49.00     H 5.30     N 10.10
Found %        49.07       5.50       9.85

EXAMPLE 2

Preparation of S-(2-pyridyl N-oxide) glutathione

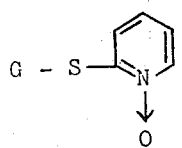

wherein G — glutathione residue.

First Method

To a suspension of 0.5 g of glutathione in a mixture of 20 cc of dioxane and 20 cc of methanol, there is added 0.5 cc of triethylamine and the whole is brought to a boil.

The 0.2 g of 2-chloro pyridine N-oxide is added and the solution obtained is then heated for 30 minutes with reflux. 0.2 cc of triethylamine is then added and the resulting mixture is again brought to reflux for an hour.

The solution is concentrated to dryness and the residue is dissolved several times with ethanol. It is washed with water until the absence of chloride ions is detected and then filtered. Thus, 0.45 g of a white product, having a melting point of 230°C, is collected.

Second Method

To a solution of 10 moles of glutathione in 50 cc of methanol and 2.5 cc of concentrated ammonia, there are added 1.3 g of 2-chloropyridine N-oxide in 20 cc of methanol. The solution is first heated for an hour with reflux and again for an additional hour, after subsequent addition of 1 cc of ammonia. The reaction mixture is then acidified by addition of HCl and is concentrated to dryness. The gummy residue is dissolved with ethanol and yields 2.95 g of white solid exhibiting the same characteristics as in the first method above.

Third Method

To a solution of 3.07 g of glutathione in 30 cc of water and 2.5 cc of concentrated ammonia, there are added 1.5 g of 2-chloro pyridine N-oxide and the solution is left for 6 hours at ambient temperature. 1.25 cc of ammonia are then added and the resulting mixture is allowed to stand over night. It is then concentrated to dryness under vacuum. The resulting residue is dissolved with ethanol, filtered and washed with water, yielding 2.65 g of the above product.

By chromatography on paper in a phenol-water medium, there is obtained an $R_f = 0.90$.

| Analysis: $C_{15}H_{20}N_4O_7S$ | | | | |
|---|---|---|---|---|
| Calculated % | 44.99 | H 5.03 | N 13.99 | S 8.01 |
| Found % | 44.92 | 5.15 | 14.01 | 8.20 |

EXAMPLE 3

Preparation of S-[(2)-2-pyridyl ethyl] glutathione

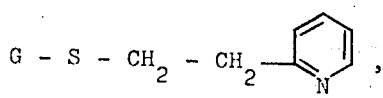

wherein G = glutathione residue.

A solution of 1.05 g of 2-vinyl pyridine in 20 cc of methanol is added to a solution of 3.07 g of glutathione in 100 cc of methanol and 2.5 cc of concentrated ammonia. The mixture is first stirred for 4 hours at ambient temperature and then acidified to a pH 3 by the addition thereto of hydrochloric acid. The resulting mixture is then concentrated to dryness under vacuum and the resulting residue is first dissolved with methanol, filtered and then washed with methanol until the absence of chloride ions is detected. 2.7 g of the above product is obtained exhibiting a melting point of around 240°C (with decomposition).

By chromatography on paper in a phenol-water medium there is obtained on $R_f = 0.85$.

| Analysis: $C_{17}H_{24}N_4O_6S$ | | |
|---|---|---|
| Calculated % | N 13.58 | S 7.77 |
| Found % | 13.51 | 7.96 |

EXAMPLE 4

Preparation of S,S'-(2,2'-sulfonyl diethyl) diglutathione

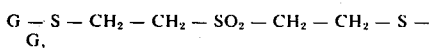

wherein G = glutathione residue.

To a solution of 10 m moles of glutathione in 50 cc of water there is added, drop by drop, 0.59 g of divinyl sulfone. The resulting mixture is then allowed to stand over night at ambient temperature after which it is concentrated to dryness. The resulting residue is then washed with ethanol, yielding 2.3 g of the above product which exhibits a melting point of 250°C with decomposition.

By chromatography on paper in a phenol-water medium, there is obtained an $R_f = 0.30$.

| Analsis: $C_{24}H_{40}N_6O_{14}S_3$ | | |
|---|---|---|
| Calculated % | N 11.47 | S 13.13 |
| Found % | 11.64 | 13.08 |

EXAMPLE 5

Preparation of S-(1,2-dicarboxy ethyl) glutathione

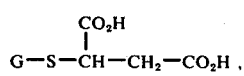

wherein G = glutathione residue.

First Method

To a mixture of 0.5 g of glutathione, 20 cc of dioxane, 20 cc of methanol and 0.68 cc of triethylamine brought to the boil, there is added over a 15 minute period a solution of 0.19 g of maleic acid in 5 cc of methanol. Reflux heating is continued for an hour and then the solution is concentrated to dryness. The resulting residue is washed with ethanol and then filtered, yielding 0.55 g of a white, water-soluble product, exhibiting a poorly defined melting point (beginning of decomposition around 150°C).

Second Method

To an aqueous solution of glutathione (3.07 g of glutathione in 100 cc of water) there is added, drop by drop, a solution of 1.16 g of maleic acid in 50 cc of water. The resulting mixture is heated at 50°C for 3 hours and then concentrated to dryness, yielding 3.2 g of the above product which exhibits a melting point having essentially the same characteristics as that achieved in the first method.

By chromatography on paper in a phenol-water medium, there is obtained an $R_f = 0.35$.

Analysis: $C_{14}N_{21}N_3O_{10}S$
Calculated % S 7.57
Found % 7.50

EXAMPLE 6

Preparation of S-(β-aminoethyl) glutathione $G - S - CH_2 - CH_2 - NH_2$, wherein G = glutathione residue.

There are added over a 5 minute period 1.29 g of ethylene imine, freshly distilled, to a solution of 30 millimoles of glutathione in 150 cc of water. The resulting mixture is stirred for ten minutes at ambient temperature and then concentrated to dryness. The resulting solid residue is triturated and washed successively with benzene, ethanol and acetone. The white product thus obtained (9.5 g) melts around 200° with decomposition.

Analysis: $C_{12}H_{22}N_4O_6S$
Calculated %  C 41.13   H 6.33   N 15.99   S 9.15
Found %       40.88     6.44     15.88     8.90

V EXAMPLES OF TOPICALLY APPLIED COMPOSITIONS

EXAMPLES 7 – 9

A hair lotion composition according to the invention is prepared by mixing:

| | |
|---|---|
| S-(1,2-dicarboxy ethyl) glutathione | 1.5 g |
| Ethyl alcohol, 50° titer, q.s.p. | 100 cc |
| Perfume | 0.1 |
| Dye | 0.1 g |

Essentially similar effective hair lotion compositions are produced by replacing the S-(1,2-dicarboxy ethyl) glutathione with S-isopropyl glutathione and S-allyl glutathione.

EXAMPLES 10 – 12

A hair lotion composition according to the invention is prepared by mixing:

| | |
|---|---|
| S-decyl glutathione | 3 g |
| Ethyl alcohol, 70° titer, q.s.p. | 100 cc |

Essentially similar effective hair lotion compositions are produced by replacing the S-decyl glutathione with S-n-octyl glutathione and S-hexadecyl glutathione.

EXAMPLES 13 – 15

A lotion for use in treating greasy hair is prepared by dissolving 0.15 g of S-(p-bromobenzyl) glutathione in 100 cc of ethyl alcohol, 50° titer.

Essentially similar effective lotions are prepared by replacing the S-(p-bromobenzyl) glutathione with S-(p-methoxybenzyl) glutathione and S-(p-butoxybenzyl) glutathione.

EXAMPLES 16 – 18

A fluid hair-dressing gel is prepared by mixing:

| | |
|---|---|
| S-(2-pyridyl N-oxide) glutathione | 0.5 g |
| Carboxy vinyl polymer-carboxy polymethylene sold under the tradename CARBOPOL 934 | 0.45 g |
| Polyvinylpyrrolidone (m.W. 40,000) | 2 g |
| Lanolin oxyethylenated with 16 moles ethylene oxide | 1 g |
| Polyethylene glycol (M.W. 300) | 305 g |
| Methyl p-hydroxybenzoate | 0.1 g |
| Propyl p-hydroxybenzoate | 0.1 g |
| Perfume | 0.1 g |
| Triethanolamine, q.s.p. pH 8 | |
| Water, q.s.p. | 100 cc |

Essentially similar effective hair-dressing gels are produced by replacing the S-(2-pyridyl N-oxide) glutathione with S-(3,3-ethylenedioxy propyl) glutathione and S-furfuryl glutathione.

EXAMPLES 19 – 21

The following solution is prepared:

| | |
|---|---|
| Polyvinylpyrrolidone vinyl acetate resin sold under the tradename of "E 335" by the General Anilin Company K (1% ethanol solution) = 25-35 | 10 g |
| S-dodecyl glutathione | 0.5 g |
| Methylchloroform | 15 g |
| Absolute ethyl alcohol, q.s.p. | 100 g |

To prepare a lacquer for greasy hair, 30 g of said solution are packaged in an aerosol bomb also containing 49 g of trichlorofluoromethane and 21 g of dichlorodifluoromethane.

This lacquer applied regularly to greasy hair makes it possible progressively to reduce its greasy appearance.

This lacquer also has all the qualities of a good hair lacquer.

Essentially similar effective hair lacquers in aerosol form are produced by replacing the S-dodecyl glutathione with S-(3,3-diethoxy propyl) glutathione and S-p-butylthiobenzyl glutathione.

EXAMPLES 22 – 24

A liquid shampoo is prepared as follows:

| | |
|---|---|
| Sodium lauryl sulfate oxyethylenated with 2.2 moles of ethylene oxide | 9 g |
| Sodium monolauryl sulfoccinate | 1 g |
| Polyethylene glycol distearate | 2 g |
| Lauryl diethanolamide | 2 g |
| S-(β-aminoethyl) glutathione | 2 g |
| Perfume | 0.3 g |
| Triethanolamine, q.s.p. pH 6.5 | |

| | |
|---|---|
| Water, q.s.p. | 100 g |

Essentially similar effective shampoo formulations are prepared by replacing S-(β-aminoethyl) glutathione with S-(2-carboxy-2-octadecanamido ethyl) glutathione and S-(methane 2-sulfoamido ethyl) glutathione.

EXAMPLES 25 – 27

A cream shampoo is prepared as follows:

| | |
|---|---|
| Sodium lauryl sulfate | 12 g |
| "Hostapon C.T.", a compound of the formula: R—CO—N—(CH$_2$)$_2$SO$_3$Na CH$_3$, wherein R is a radical derived from copra fatty acids | 40 g |
| Lauryl monoethanolamide | g |
| Glycerol monostearate | 4 g |
| S-(β-carboxyethyl) glutathione | 3 g |
| Lactic acid, q.s.p. pH = 6.5 | |
| Perfume | 0.2 g |
| Water, q.s.p. | 100 g |

Essentially similar effective cream shampoo formulations are prepared by replacing S-(β-carboxyethyl) glutathione with S-(2-carboxy 2-ureido ethyl) glutathione and S-(2-carboxy 2-hexadecanamido ethyl) glutathione.

EXAMPLES 28 – 30

A powder shampoo is prepared by making the following mixture:

| | |
|---|---|
| Sodium lauryl sulfate | 40 g |
| Hostapon K.A., a compound having the formula: R—COO—(CH$_2$)$_2$—SO$_3$Na, wherein R is radical derived from copra fatty acids | 39 |
| S-benzylglutathione | 20 g |
| Perfume | 1 g |

Essentially similar effective shampoo formulations, in powder form, are prepared by replacing S-benzyl-glutathione with S-(5-nitro 2-pyridyl) glutathione and S-pyrrolidinocarbonylmethyl glutathione.

EXAMPLES 31 – 33

The first stage, i.e., the reducing stage of a permanent waving operation is performed with a reducing composition containing:

| | |
|---|---|
| Ammonium thioglycolate | 9.5 g |
| Polyethoxyester of fatty alcohol (ethyl alcohol 30%-stearyl alcohol 70%) sold under the tradename SIPOL WAX AO | 0.8 g |
| Ammonia solution, q.s.p. 0.7 N | |
| Water, q.s.p. | 100 g |

A two-package neutralizing composition is then employed, the first package containing:

| | |
|---|---|
| Hydrogen peroxide, q.s.p. 6.6 volumes | |
| Citric acid | 0.1 g |
| Water, q.s.p. | 100 cc | and the second package containing

| | |
|---|---|
| S-(carboxymethyl) glutathione (powder) | 5 g |

The powder, constituting the second part, is dissolved in the hydrogen peroxide solution and the hair previously treated with the above reducing agent and still wound on curlers is treated with the resulting neutralizing solution for a time sufficient to reform the disulphide bonds in the keratin of the hair.

After the hair has been rinsed, unwound from the curlers and dried, a permanent is obtained, which exhibits good holding characteristics. Equally important, however, is that the hair remained non-oily in appearance for a significantly longer time than did the hair when permanently waved using essentially the same neutralizing composition but without the compound of this invention.

Essentially similar effective neutralizing compositions are prepared by replacing S-(carboxymethyl) glutathione with S-(p-phenoxybenzyl) glutathione and S-(β-phenylethyl) glutathione.

EXAMPLES 34 – 36

A single stage permanent waving operation on hair exhibiting a greasy appearance is effected with a solution having the following composition:

| | |
|---|---|
| Glycol thioglycolate | 6 g |
| Glycol dithiodiglycolate | 10 g |
| S-(2-(2)-pyridyl ethyl) glutathione | 1 g |
| Ammonia, q.s.p. pH 9.5 | |
| Water, q.s.p. | 100 cc |

After the hair has been shampooed and dried, each lock is impregnated with said solution then put up in curlers of averge diameter. When the hair has been put up in curlers, all the locks are saturated with the same solution, the head is covered with a cap and left for a period of 20 to 25 minutes. Thereafter the hair is carefully rinsed with plenty of warm water. The curlers are then removed and the hair rinsed again. The curling obtained is quite marked and supple and the hair becomes greasy much more slowly than before.

Essentially similar effective single stage permanent waving compositions are prepared by replacing S-(2-(2)-pyridyl ethyl) glutathione with S-(octadecene-9yl) glutathione and S-(2,2-dimethoxy ethyl glutathione).

EXAMPLES 37 – 39

An anti-acne cream for application on the skin is prepared by mixing:

| | |
|---|---|
| S-octadecyl glutathione | 5 g |
| Cetyl-stearyl alcohol oxyethylenated with 15 mols ethylene oxide | 7 g |
| Silicone oil (dimethylpolysiloxane having a viscosity of 20 – 22° at room temperature) | 1 g |
| Diethylene glycol stearate | 6 g |
| Methyl p-hydroxybenzoate | 0.1 g |
| Propyl p-hydroxybenzoate | 0.1 g |
| Water, q.s.p. | 100 cc |

Essentially effective creams for the skin are prepared by replacing S-octadecyl glutathione by S,S′-

(2,3-dihydroxy 1,4-butanediyl) glutathione and S-(2-pyridyl methyl) glutathione.

Examples 40 – 43

An anti-acne milk is prepared by mixing:

| | |
|---|---|
| S-(o-fluorobenzyl) glutathione | 0.5 g |
| Carboxy vinyl polymer-carboxy polymethylene sold under the tradename CARBOPOL 934 | 0.375 g |
| Isopropyl ester of lanolin fatty acids | 1 g |
| Lanolin oxyethylenated with 16 moles ethylene oxide | 2.5 g |
| Cetyl-stearyl alcohol oxyethylenated with 15 moles ethylene oxide | 3 g |
| Substituted alkylamide | 2 g |
| Isopropyl alcohol | 20 cc |
| Triethanolamine, q.s.p. pH 8 | |
| Methyl para-hydroxybenzoate | 0.1 g |
| Propyl para-hydroxybenzoate | 0.1 g |
| Water, q.s.p. | 100 cc |

Essentially similar effective anti-acne milk formulations are prepared by replacing S-(o-fluorobenzyl) glutathione, S-(p-chlorobenzyl) glutathione and S(m-chlorobenzyl) glutathione.

Examples 44 – 47

An anti-acne milk is prepared by mixing:

| | |
|---|---|
| S-(β-ureidoethyl) glutathione | 2 g |
| Carboxy vinyl polymer-carboxy polymethylene sold under the tradename of CARBOPOL 934 | 0.375 g |
| Isopropyl ester of lanolin fatty acid | 1 g |
| Lanolin oxyethylenated with 16 moles ethylene oxide | 2.5 g |
| Cetyl-stearyl alcohol oxyethylenated with 15 moles ethylene oxide | 3 g |
| Substituted alkylamide | 2 g |
| Ethyl alcohol | 20 cc |
| Triethanolamine, q.s.p. pH 8 | |
| Methyl p-hydroxybenzoate | 0.1 g |
| Propyl p-hydroxybenzoate | 0.1 g |
| Water, q.s.p. | 100 g |

Essentially similar effective anti-acne milk formulations are prepared by replacing S-(β-ureidoethyl) glutathione by S-(diphenylmethyl) glutathione S-(β-phenylacetamidoethyl) glutathione and S-(m-chlorobenzamidoethyl) glutathione.

VI EXAMPLES OF ORALLY ADMINISTERED COMPOSITIONS

EXAMPLES 48 – 50

The following composition is prepared and is usefully employed to reduce excessive secretion of sebum on the scalp. It is orally administered in the form of drops.

| | |
|---|---|
| S-[(2)-2-pyridyl ethyl] glutathione | 1 g |
| Glycerin | 40 g |
| Ethyl alcohol | 30 g |
| Water, q.s.p. | 100 g |
| Lemon tincture (sufficient for flavor) | |

The oral administration of this composition at a rate of 10 drops per day for 15 days to a person having greasy hair due to excessive secretion of sebum substantially improves the condition of the scalp and the appearance of the hair.

Essentially similar effective results are obtained when S-[(2)-2-pyridyl ethyl] glutathione is replaced with the following compounds:

S-[2-carboxy 2-(9-octadecene amido) ethyl] glutathione and S-(2-tetradecanamido ethyl) glutathione.

EXAMPLES 51 – 53

The following composition, intended to be administered orally in drop form, is prepared by mixing:

| | |
|---|---|
| S-(o-tolyl) glutathione | 0.75 g |
| Glycerin | 40 g |
| Ethyl alcohol | 30 g |
| Water, q.s.p. | 100 g |
| Lemon tincture (sufficient for flavoring) | |

Oral administration of this composition at a rate of 10 drops per day for 15 days to a person having greasy hair due to excessive secretion of sebum, substantially improves the condition of the scalp and the appearance of the hair.

Essentially similar effective results are obtained when S-(o-tolyl) glutathione is replaced by S-(2-carboxy-2-propionamido ethyl) glutathione and S-octyl-N-hexadecanoyl glutathione.

EXAMPLES 54 – 56

The following composition, for oral administration in drop form, is prepared by mixing:

| | |
|---|---|
| S-(2-thenyl) glutathione | 0.1 g |
| Glycerine | 40 g |
| Ethyl alcohol | 30 g |
| Water, q.s.p. | 100 g |
| Lemon tincture (sufficient for flavoring) | |

Oral administration of this composition at a rate of 10 drops per day for 15 days to a person having greasy hair due to excessive secretion of sebum substantially improves the condition of the scalp and the appearance of the hair.

Essentially similar effective results are obtained when S-(2-thenyl) glutathione is replaced by S-[2-(10-undecene amido) ethyl] glutathione and S-(cyclohexyl-benzyl) glutathione.

EXAMPLES 57 – 59

Ampoules, each containing the following composition, are prepared:

| | |
|---|---|
| S-[(2)-2-pyridyl ethyl] glutathione | 50 mg |
| Glucose | 300 mg |
| Water, q.s.p. | 5 ml |
| Orange juice (sufficient for flavoring) | |

The oral administration of this composition at rate of 2 ampoules each day for 15 days to a person having greasy hair due to excessive secretion of sebrum substantially improves the condition of the scalp and the appearance of the hair.

Essentially similar effective results are achieved by replacing S-[(2)-2-pyridyl ethyl] glutathione by S-(2-trifluoracetamido ethyl) glutathione and S-benzyl N-carbamyl glutathione.

EXAMPLES 60 – 62

Ampolues, each containing the following composition, are prepared:

| | |
|---|---|
| S-(β-carboxyethyl) glutathione | 50 mg |
| Glucose | 300 mg |
| Water, q.s.p. | 5 ml |
| Orange juice (sufficient for flavor) | |

Oral administration of this composition at a rate of 2 ampoules per day for 15 days to a person having greasy hair due to excessive secretion of sebum substantially improves the condition of the scalp and the appearance of the hair.

Essentially similar effective results are achieved by replacing S-(β-carboxyethyl) glutathione by S-(cyclohexylbenzy) glutathione and S-β-hydroxyethyl glutathione.

EXAMPLE 63

Ampoules are prepared, each containing the following composition:

| | |
|---|---|
| S-phenyl glutathione | 50 mg |
| Glucose | 300 mg |
| Water sufficient for | 5 ml |
| Orange juice (sufficient for flavoring) | |

Oral administration of this composition at a rate of 2 ampoules per day for 15 days to a person having greasy hair due to excessive secretion of sebum substantially improves the condition of the scalp and the appearance of the hair.

EXAMPLES 64 – 66

Granules to be eaten are prepared, having the following composition:

| | |
|---|---|
| S-(γ-phenylpropyl) glutathione | 2.5 g |
| Saccharose | 200 g |
| Lemon syrup | 50 g |

These granules, administered at a rate of 1 teaspoon twice per day to a person having greasy hair and scalp due to excessive secretion of sebum substantially reduces excessive secretion of sebum and thereby significantly improves the condition of the scalp and the appearance of the hair.

Essentially similar effective results are achieved by replacing S-(γ-phenylpropyl) glutathione by S-(3,4-dimethoxy benzyl) N-acetyl glutathione and S-carbamoylmethyl glutathione.

EXAMPLES 67 – 69

Granules to be eaten are prepared, having the following composition:

| | |
|---|---|
| S-(piperonyl) glutathione | 2.5 g |
| Saccharose | 200 g |
| Lemon syrup | 50 g |

These granules administered at a rate of one teaspoon twice per day to a person having greasy hair and scalp due to excessive secretion of sebum substantially reduces excessive secretion and significantly improves the condition of the scalp and the apperance of the hair.

Essentially similar effective results are achieved by replacing S-(piperonyl) glutathione by S-(2,4-dichlorobenzyl) N-propionyl glutathione and S-(2-p-toluenesulfonamido ethyl) glutathione.

EXAMPLES 70 – 72

Pills to be swallowed are prepared, each having the following composition:

| | |
|---|---|
| S-(2-naphthyl) glutathione | 50 mg |
| Lactose | 300 mg |
| Aromatic gum, powder | 100 mg |
| Simple syrup, q.s.p. | 500 mg |

These pills, taken at a rate of 2 per day, by a person having greasy hair due to excessive secretion of sebum substantially improves the condition of the scalp and the appearance of the hair.

Essentially similar effective results are achieved by replacing S-(2-naphthyl) glutathione by S-(β-nicotinamidoethyl) glutathione and S-p-methylsulfinyl-benzyl glutathione.

EXAMPLES 73 – 74

Pills, intended to be swallowed, each having the following composition, are prepared:

| | |
|---|---|
| S,S'-(2,2'-sulfonyl diethyl) diglutathione | 50 mg |
| Lactose | 300 mg |
| Aromatic gum, powder | 100 mg |
| Simple syrup, q.s.p. | 500 mg |

These pills taken at a rate of two per day by a person having greasy hair due to excessive secretion of sebum substantially improves the condition of the scalp and the appearance of the hair.

Essentially similar effective results are obtained by replacing S,S'-(2,2'-sulfonyl diethyl) diglutathione by S-(2-diethylaminocarbonyl ethyl) glutathione.

EXAMPLE 75

Pills, to be swallowed, are prepared, each having the following composition:

| | |
|---|---|
| S-(2-thenyl) glutathione | 50 mg |
| Lactose | 300 mg |
| Aromatic gum, powder | 100 mg |
| Simple syrup, q.s.p. | 500 mg |

These pills, taken at a rate of two per day by a person having greasy hair due to excessive secretion of sebum substantially improves the condition of the scalp and the appearance of the hair.

What is claimed is:

1. A process for treating the scalp and skin, characterized by an excessive secretion of sebum to improve the condition thereof by reducing said excessive secretion of sebum thereby effectively reducing a greasy appearance of the hair and skin comprising topically applyng to the scalp or skin in amounts effective to substantially reduce said greasy appearance of the hair and skin a composition comprising a mixture of an inert, nontoxic carrier selected from the group consisting of water, a lower alkanol, an aqueous solution of a lower alkanol and in an amount of about 0.1 - 5 percent by weight of said composition a component selected from the group consisting of:

(i') a compound of the formula

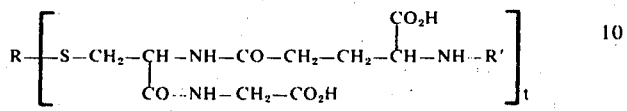

where R' is selected from the group consisting of hydrogen, —CONH$_2$ and —COA wherein A is selected from the group consisting of alkyl having 1–18 carbon atoms and alkenyl having 2 to 18 carbon atoms, and $t$ is 1 or 2 and a. when $t = 1$, R is selected from the group consisting of:
1. linear or branched alkyl having from 1 to 18 carbon atoms,
2. alkenyl having from 3 to 18 carbon atoms,
3. alkyl having from 2 to 4 carbon atoms and substituted by 1–2 hydroxy groups,
4.

wherein $m$ is 1 or 2 and R'' is lower alkyl having 1–4 carbon atoms,

5.

wherein R''' is selected from the group consisting of -CONH$_2$ and -COA wherein A has the meaning given above, 6. —(CH$_2$)$_n$—NH—R$_1$, wherein $n$ is 2 or 3 and R$_1$ is selected from the group consisting of hydrogen, —CONH$_2$, —COR$_2$ and —SO$_2$R$_3$ wherein R$_2$ is selected from the group consisting of hydrogen, alkyl having 1–18 carbon atoms, alkenyl having 2 to 18 carbon atoms, —CF$_3$, —CH$_2$—C$_6$H$_5$,

wherein R$_7$ is selected from the group consisting of hydrogen, alkyl having 1–4 carbon atoms, alkoxy having 1–4 carbon atoms and hydrogen and R$_3$ is selected from the group consisting of alkyl having 1–4 carbon atoms and

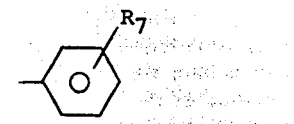

wherein R$_7$ has the meaning given above,

7. —(CH$_2$)$_p$—R$_4$ wherein $p$ is 0, 1 or 2 and R$_4$ is selected from the group consisting of
i. 1-naphthyl when $p = 0$ or 1,
ii. 2-naphthyl when $p = 0$ or 1,
iii.

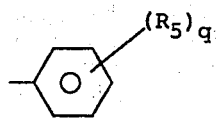

when $p = 0$, 1 or 2, wherein $q$ is 1, 2 or 3 and
a'. when $q$ is 1, 2 or 3, R$_5$ is selected from the group consisting of hydrogen, halogen, alkoxy having 1–5 carbon atoms and alkyl having 1–4 carbon atoms and
b'. when $q$ is only 1, R$_5$ is selected from the group consisting of dialkylamino wherein the alkyl moiety has 1–3 carbon atoms, phenoxy, cyclohexyl, amino, phenyl, alkylthio wherein the alkyl moiety has 1–5 carbon atoms, alkylsulfinyl wherein the alkyl moiety has 1–5 carbon atoms and trifluoromethyl, 8. —CH$_2$—CH$_2$—CH$_2$—C$_6$H$_5$,
9. —CH (C$_6$H$_5$)$_2$,
10. —CH$_2$—CH = CH - C$_6$H$_5$,
11. —CH (C$_6$H$_4$ p-OCH$_3$)$_2$,
12. —C (CH$_3$)$_2$ (C$_6$H$_4$ p-OCH$_3$),
13. —(CH$_2$)$_s$—COR$_6$ wherein $s$ is an integer of 1–4 and R$_6$ is selected from the group consisting of OH, NH$_2$, diethylamino and dimethylamino, and
14. 1,2-dicarboxyethyl b. when $t = 2$, R is selected from the group consisting of
15. —(CH$_2$)$_n$—CH$_2$— wherein $n$ is 1, 2 or 3,
16. —(CH$_2$)$_n$—CH$_2$— wherein $n$ is 1, 2 or 3 and substituted by 1 or 2 OH functions,
17. butenylene, and
18. —(CH$_2$)$_2$—SO$_2$—(CH$_2$)$_2$—, and ii'. the acid salts of the compound defined in (i').

2. The process of claim 1 wherein said composition also includes in amounts of about 4–15 percent by weight of said composition is detergent selected from the group consisting of anionic, cationic, non-ionic and amphoteric detergents, said composition having a pH of about 3–8.

3. A process for treating the scalp and skin characterized by an excessive secretion of sebum to improve the condition thereof by reducing said excessive secretion of sebum thereby effectively reducing a greasy appearance of the hair and skin comprising orally administering to a human being having a scalp or skin so characterized a composition comprising a mixture of an ingestible carrier selected from the group consisting of water, an aqueous solution of a non-toxic lower alkanol and an ingestible solid excipient and in an amount of about 1–10 percent by weight of said composition, a component selected from the group consisting of
i'. a compound of the formula

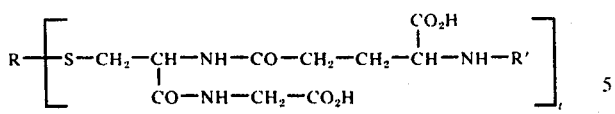

where R' is selected from the group consisting of hydrogen, —$CONH_2$ and —COA wherein A is selected from the group consisting of alkyl having 1–18 carbon atoms and alkenyl having 2 to 18 carbon atoms, and $t$ is 1 or 2 and a. when $t = 1$, R is selected from the group consisting of:
1. linear or branched alkyl having from 1 to 18 carbon atoms,
2. alkenyl having from 3 to 18 carbon atoms,
3. alkyl having from 2 to 4 carbon atoms and substituted by 1–2 hydroxy groups,
4.

wherein $m$ is 1 or 2 and R'' is lower alkyl having 1–4 carbon atoms,

5.

wherein R''' is selected from the group consisting of —$CONH_2$ and —COA wherein A has the meaning given above, 6. —$(CH_2)_n$—NH—$R_1$, wherein $n$ is 2 or 3 and $R_1$ is selected from the group consisting of hydrogen, —$CONH_2$—$COR_2$ and —$SO_2R_3$ wherein $R_2$ is selected from the group consisting of hydrogen, alkyl having 1–18 carbon atoms, alkenyl having 2 to 18 carbon atoms, —$CF_3$, —$CH_2$—$C_6H_5$,

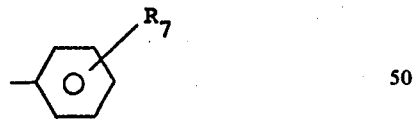

wherein $R_7$ is selected from the group consisting of hydrogen, alkyl having 1–4 carbon atoms, alkoxy having 1–4 carbon atoms and halogen and $R_3$ is selected from the group consisting of alkyl having 1–4 carbon atoms and

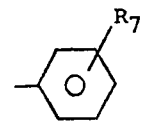

wherein $R_7$ has the meaning given above,

7. —$(CH_2)_p$—$R_4$ wherein $p$ is 0, 1 or 2 and $R_4$ is selected from the group consisting of
i. 1-naphthyl when $p = 0$ or 1,
iii. 2-naphthyl when $p = 0$ or 1,
iii.

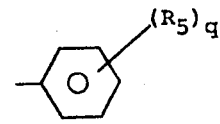

when $p = 0$, 1 or 2, wherein $q$ is 1, 2 or 3 and
a' when $q$ is 1, 2 or 3, $R_5$ is selected from the group consisting of hydrogen, halogen, alkoxy having 1–5 carbon atoms and alkyl having 1–4 carbon atoms and
b'. when $q$ is only 1, $R_5$ is selected from the group consisting of dialkylamino wherein the alkyl moiety has 1–3 carbon atoms, phenoxy, cyclohexyl, amino, phenyl, alkylthio wherein the alkyl moiety has 1–5 carbon atoms, alkylsulfinyl wherein the alkyl moiety has 1–5 carbon atoms and trifluoromethyl, 8. —$CH_2$—$CH_2$—$CH_2$—$C_6H_5$,
9. —CH $(C_6H_5)_2$,
10. —$CH_2$—CH = CH — $C_6H_5$,
11. —CH $(C_6H_4$ p-$OCH_3)_2$,
12. —C $(CH_3)_2$ $(C_6H_4$ p-$OCH_3)$,
13. —$(CH_2)_s$—$COR_6$ wherein $s$ is an integer of 1–4 and $R_6$ is selected from the group consisting of OH, $NH_2$, diethylamino and dimethylamino, and
14. 1,2-dicarboxyethyl b. when $t = 2$, R is selected from the group consisting of
15. —$(CH_2)_n$—$CH_2$— wherein $n$ is 1, 2 or 3,
16. —$(CH_2)_n$—$CH_2$— wherein $n$ is 1, 2 or 3 and substituted by 1 or 2 OH functions,
17. butenylene, and
18. —$(CH_2)_2$—$SO_2$—$(CH_2)_2$—, and (ii') the acid salts of the compound defined in (i').

* * * * *